(12) United States Patent
Daum et al.

(10) Patent No.: US 8,123,697 B2
(45) Date of Patent: Feb. 28, 2012

(54) METHOD AND APPARATUS FOR MR-GUIDED BIOPSY

(75) Inventors: Wolfgang R. Daum, Groton, MA (US); Axel Winkel, Schwerin (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 112 days.

(21) Appl. No.: 12/341,748

(22) Filed: Dec. 22, 2008

(65) Prior Publication Data

US 2009/0247859 A1 Oct. 1, 2009

Related U.S. Application Data

(63) Continuation-in-part of application No. 10/366,831, filed on Feb. 14, 2003, now abandoned.

(60) Provisional application No. 60/357,205, filed on Feb. 14, 2002, provisional application No. 61/016,300, filed on Dec. 21, 2007.

(51) Int. Cl.
*A61B 10/00* (2006.01)

(52) U.S. Cl. ...................................................... 600/562
(58) Field of Classification Search .......... 600/562–568, 600/407, 410, 411, 414, 415, 420, 421
See application file for complete search history.

(56) References Cited

U.S. PATENT DOCUMENTS 5,441,042 A 8/1995 Putman
(Continued)

*Primary Examiner* — Jeffrey G Hoekstra

(57) ABSTRACT

An MR-guided biopsy, for example, prostate biopsy, is performed by a mechanical tool for stabilizing the patient in prone position and for guiding the biopsy needle into defined targeted lesions in the prostate gland. The patient can lay prone in the MRI. The apparatus can guide an MR-visible, sterile needle sleeve, which can have a hollow tube filled with contrast media, through the anus onto the inner wall of the colon. Due to the visibility of the contrast media in the sleeve, the apparatus can be guided to the exact position. The sleeve can incorporate a tube within the contrast media filled sleeve to insert the biopsy needle and to push this needle forward into the prostate. The apparatus can utilize various mechanical mechanisms to stereotactically move the needle or needle sleeve in various directions.

31 Claims, 6 Drawing Sheets

U.S. PATENT DOCUMENTS

| | | | |
|---|---|---|---|
| 5,868,757 A | 2/1999 | Koutrouvelis | |
| 5,895,401 A * | 4/1999 | Daum et al. | 606/167 |
| 6,079,681 A | 6/2000 | Stern et al. | |
| 6,119,032 A * | 9/2000 | Martin et al. | 600/411 |
| 6,120,517 A * | 9/2000 | Daum et al. | 606/167 |
| 6,152,933 A * | 11/2000 | Werp et al. | 606/130 |
| 6,238,355 B1 * | 5/2001 | Daum | 600/567 |
| 6,274,965 B1 * | 8/2001 | Daum et al. | 310/323.11 |
| 6,470,204 B1 | 10/2002 | Uzgiris et al. | |
| 6,557,558 B1 | 5/2003 | Tajima et al. | |
| 6,558,337 B2 * | 5/2003 | Dvorak et al. | 600/564 |
| 6,574,497 B1 | 6/2003 | Pacetti | |
| 6,758,824 B1 | 7/2004 | Miller et al. | |
| 6,853,856 B2 | 2/2005 | Yanof et al. | |
| 2003/0036766 A1 * | 2/2003 | Engelhard et al. | 606/130 |

* cited by examiner

METHOD AND APPARATUS FOR MR-GUIDED BIOPSY

CROSS-REFERENCE TO RELATED APPLICATION(S)

The present application is a continuation-in-part of U.S. application Ser. No. 10/366,831, filed Feb. 14, 2003 now abandoned, which claims the benefit of U.S. Provisional Application Ser. No. 60/357,205, filed Feb. 14, 2002, the present application also claims priority of U.S. Provisional Application Ser. No. 61/016,300, filed Dec. 21, 2007, which are hereby incorporated by reference herein in their entirety, including any figures, tables, or drawings.

FIELD OF INVENTION

The subject invention pertains to a method and apparatus for MR-guided biopsy. The subject invention can be applied to prostate biopsy. In a specific embodiment, the subject invention relates to a stereotactic positioning device for MR-guided interventions, such as biopsies of suspicious areas of the prostate gland. MRI (magnetic resonance imaging) is a current radiological imaging modality to view soft tissue lesions of the human body. MR can be used to guide the subject positioning device to directly puncture lesions in the prostate and/or to biopsy these.

BACKGROUND OF THE INVENTION

Prostate cancer is the most common cancer, excluding skin cancers, in American men. The American Cancer Society estimates that during 2002 about 189,000 new cases of prostate cancer will be diagnosed in the United States. Accurate determination of the extent of local disease in the prostate is difficult. Current imaging techniques include, for example, transrectal ultrasound (TRUS), endorectal coil magnetic resonance imaging (MRI), and proton magnetic resonance spectroscopic imaging (MRSI). The reported accuracy of TRUS for determining if prostate cancer is confined within the capsule varies widely from 58% to 90%. However, preliminary data from recent studies of endorectal MRI show higher accuracy (75-90%) than TRUS, and better consistency.

In addition to morphologic extent, directed biopsy and assessment of tumor aggressiveness are important for accurate staging and treatment for prostate cancer when there is an elevated PSA. Current biopsy techniques are based on random spatial sampling and have a lower than desired sensitivity (60-70%) for identification of carcinoma of the prostate. Early preliminary studies of combined MRI/MRSI demonstrated localization of cancer to a sextant of the prostate with sensitivity up to 95% and specificity up to 91%. However, more specifically localized biopsies, rather than randomly taken biopsies, would be desirable.

MRI is presently regarded as the best imaging modality for assessing soft-tissue tumors like prostate cancer. This is confirmed by numerous reports in the literature. In an early study, carried out from December 1987 to April 1989, Rifkin et al [7] report on the collaborative effort of five institutions that are part of the Radiological Diagnostic Oncology Group. More than 200 patients who were thought clinically to have localized cancer of the prostate were studied preoperatively with both MRI and transrectal ultrasonography to evaluate the ability of these techniques to determine the exterit (stage) of the tumor. They underwent radical prostatectomy, and radiologic and pathological findings were correlated. The overall staging accuracy of ultrasonography was 58% (126 of 219 patients), with a standard error of 3%. The overall staging accuracy of MRI was 69% (133 of 194 patients), with a standard error of 3%. The subject invention can increase the diagnostic accuracy of MRI when combining MRI scans with interventional biopsy techniques.

Prostate cancer is the second most common cause of cancer death in US men. Its incidence is on the rise because more cancers are detected due to wide-ranging screening programs using either digital rectal exams or serum prostate-specific antigen (PSA). Whenever abnormalities crop up in these examinations, the patient is traditionally referred for ultrasound-guided biopsy, which has a low sensitivity and a specificity of only 60% for cancer detection [3]. This is why ultrasound is often used just to guide biopsies. However, MRI performs much better at cancer detection.

Typical prostate biopsies are performed by palpation (whether or not a nodule is present) or using ultrasound guidance (when a visible lesion is present). However, endorectal ultrasound is not sensitive enough for a screening tool. The visibility of the anterior capsule is poor as is visualization of seminal vesicle and lymph node involvement. Extracapsular disease and lymph node involvement is better picked up with MR, although interobserver variability is quite high (positive predictive value ~70%). PSA and proton MR spectroscopy get higher ratings for predicting the Gleason grade. Patients with incompatible PSA and biopsy results or MR spectroscopy results or with MR visible lesions would thus benefit from an MR guided prostate biopsy.

BRIEF SUMMARY OF INVENTION

The subject invention pertains to a method and apparatus for MR-guided biopsy. The subject invention can be applied to, for example, prostate biopsy. In a specific embodiment, the subject invention can provide a mechanical tool for stabilizing the patient in prone position and to guide a biopsy needle into defined targeted lesions in the prostate gland. The patient can lay prone in the MRI. The subject apparatus can guide an MR-visible, sterile needle sleeve, which can have a hollow tube filled with contrast media, through the anus onto the inner wall of the colon. Due to the visibility of the contrast media in the sleeve, the apparatus can be guided to the exact position. The sleeve can incorporate a tube within the contrast media filled sleeve to insert the biopsy needle and to push this needle forward into the prostate. The subject apparatus can utilize various mechanical means to stereotactically move the needle or needle sleeve in various directions.

DETAILED DESCRIPTION OF THE INVENTION

The subject invention pertains to a method and apparatus for MR-guided biopsy. In a specific embodiment, the subject invention can be utilized for prostate biopsy. In a specific embodiment, the subject invention relates to a positioning device for prostate interventions, which can incorporate many parts, such as a biopsy needle, a needle sleeve, various positioning and adjustment parts, coils, and more.

Figure 1:
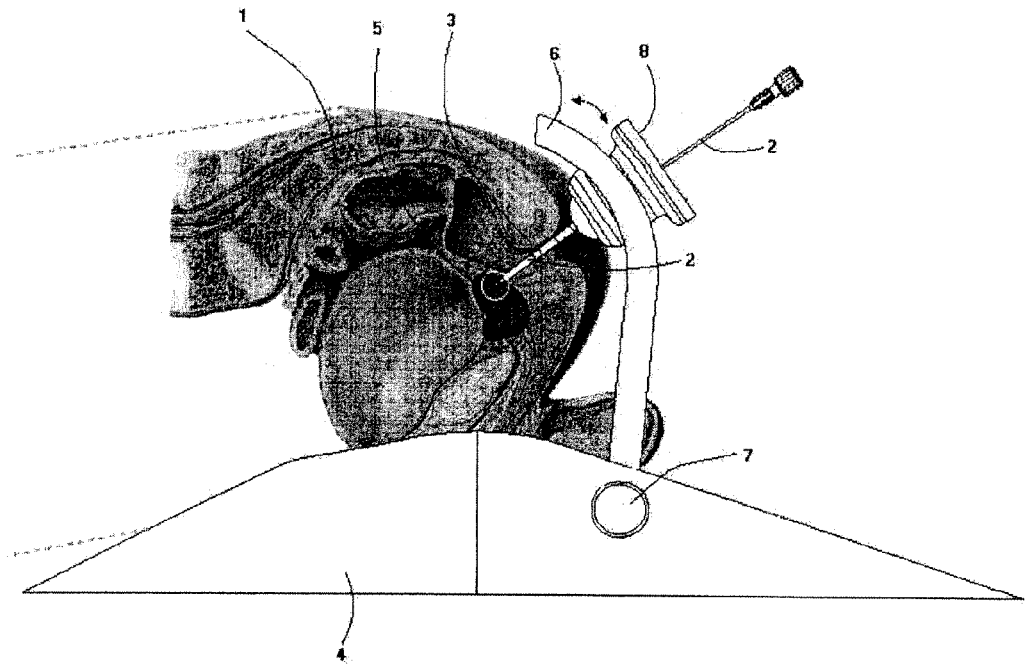
FIG. 1 illustrates a prostate biopsy system in accordance with the subject invention, patient lying prone.

FIG. 1 illustrates a specific embodiment of the subject prostate biopsy system in use with a patient. The patient 1 is lying in a prone position and the biopsy needle 2 is introduced endorectally through the anus 3. A specially shaped positioning device 4 is positioned under the patient's hips to stabilize the patient as needed for the procedure. Positioning device 4 can provide cushion to the patient. In this position the patient's back side is lifted up a little, so that the physician has better access through the patient's anus 3. In FIG. 1 the biopsy needle 2 is directly inserted through the anus 3 of the patient through the intestine wall of the rectum directly into the prostate. Here no special introducer device, as described is used. On the positioning device 4 is mounted a holding arm 6, which is movable around an axis 7 and is adjustable in height. Attached to the holding arm 6 is the needle holder 8 through which the biopsy needle 2 will slide.

There are two ways to operate this embodiment, and later described prostate biopsy embodiments, in conjunction with magnetic resonance imaging (MRI). In a first technique the patient is pulled out from the MR magnet to operate the device, pushed back in the magnet to control the position of the needle guide, and pulled out from the magnet for further needle adjustments if needed. The dimensions for the necessary corrections can be taken from the image and transferred to the scales of the device. In a second technique, the patient stays in the magnet and images are taken during the needle repositioning procedure. The device will appear in the image and is operated from the outside by simply reaching in with the arm of the operator or by remotely operated tools. These tools can be, for example, long plastic sticks 9. Sticks 9 can be between 50 cm and 150 cm long, and 5 mm to 20 mm in diameter. Sticks 9 can have a grip 10 on the proximal end and a tool 11 at the distal end to attach to a particular part of the prostate biopsy device. The attachment tool 11 can, for instance, attach directly to the grip of the biopsy needle 2 for the purpose of adjusting the position and pushing the needle 2 into the tissue. The attachment tool 11 can be changed to attach to different parts. The stick 9 can be extended in length during the operation or there can be sticks of various defined preset lengths.

Figure 2:
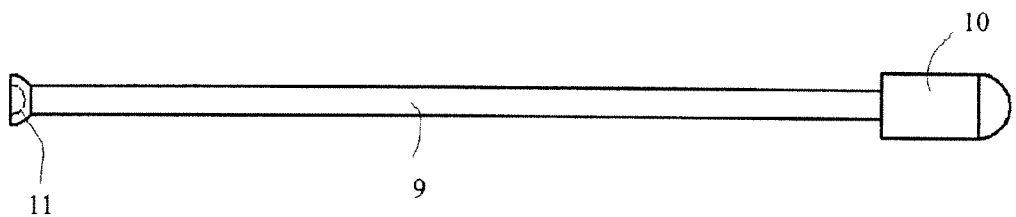
FIG. 2 illustrates a stick to remotely operate the embodiment of FIGS. 3A-4D and others of the subject device from outside the MR magnet.
Figure 3A:
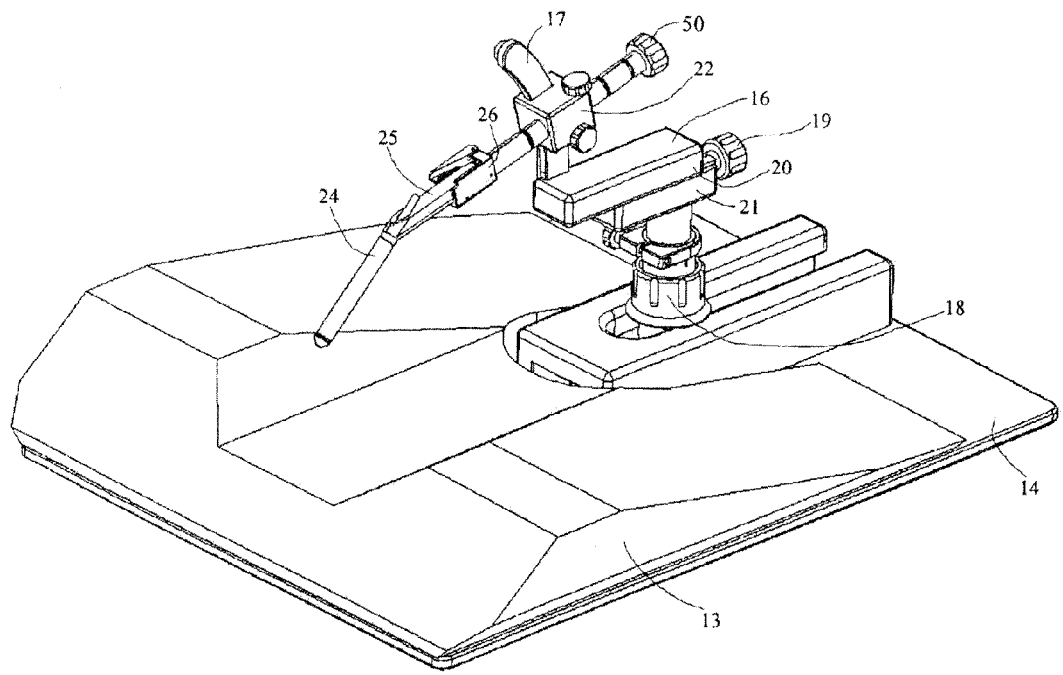
FIG. 3A illustrates a three dimensional view of an embodiment of the subject invention, from a more frontal point of view.
Figure 3B:
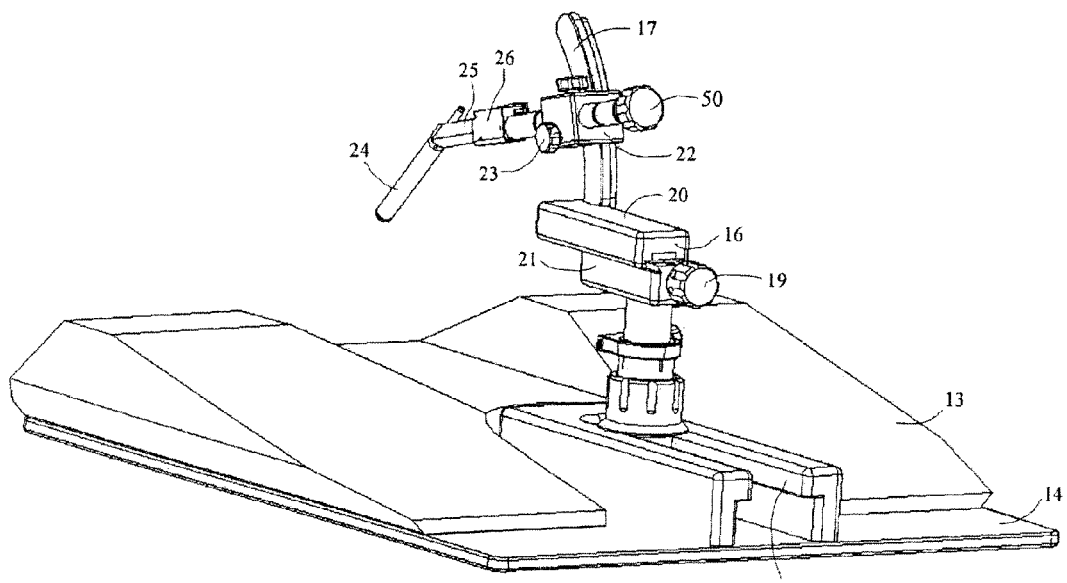
FIG. 3B illustrates a three dimensional view of the embodiment of FIG. 3A of the subject invention, from a more back point of view.

FIG. 3 shows another embodiment of the subject invention. FIG. 3A shows the device from a frontal view, while FIG. 3B shows the device from a rear view. Positioning device 13 is mounted on the base plate 14. Positioning device 13 can also provide cushion for the patient. The arm of the device, including lower arm 16 and upper arm 17, is locked in the arm-mounting-track 15 of the base plate 14 by arm-mounting-lock-bolt 18. Operating the adjustment-screw 19 allows the lower arm 16 to lengthen or shorten itself by means of a spiral-drive, not further shown here, within the lower arm 16. The spiral-drive moves the sliding-part 20 of the lower arm 16 against the fixed base-part 21 of the lower arm 16. The upper arm 17 is fixed on the distal end of the sliding-part 20 of the lower arm 16 and is designed to be a curved track for the needle-sleeve-holder 22. The needle-sleeve-holder 22 slides up and down the curved upper arm 17 and locks in the desired position via a locking mechanism, operated with lock-bolt 23. The curved upper arm 17 allows the movement of the needle-sleeve around a pivot point. In a specific embodiment, the pivot point is the anus 3, such that the patient can be positioned and the subject device adjusted so that as the needle-sleeve-holder 22 slides up and down the curved upper arm 17 the needle-sleeve moves about a pivot point, with the pivot point being the patient's anus. The needle sleeve 24 with needle-sleeve-block 25 can be a disposable device and can be changed via the needle-sleeve-lock-in mechanism 26, not further shown here. The needle sleeve 24 and needle-sleeve-block 25 can be moved forward and backwards via a spiral-drive mechanism, not further shown in detail here, by operating screw 50. This whole prostate-biopsy-device can be a reusable, and at least a cleanable, but most likely a sterilizeable unit. Screws, such as adjustment screw 19 or operating screw 50, can be reached and operated with a stick 9, as shown in FIG. 2. Special adapting tools 11 are designed, but not further described here. In another embodiment of the invention, which is not further shown here, these screws are not manually operated, but motor operated with MR compatible motors such as piezo electric motors described in U.S. Pat. No. 6,274,965.

Figure 4A:
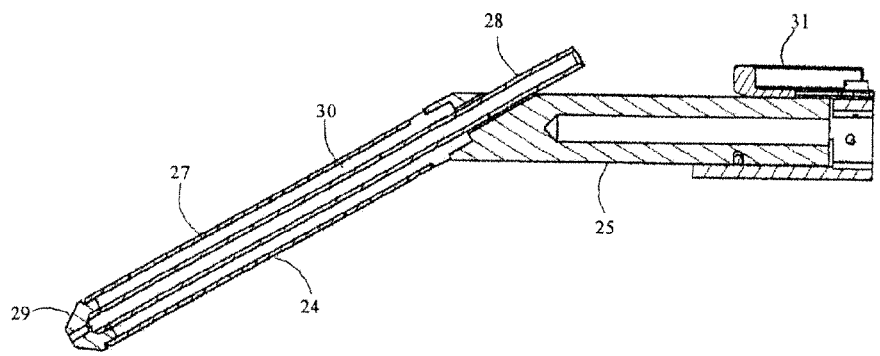
FIG. 4A illustrates a cross-sectional view of disposable needle-sleeve and needle-sleeve-block of FIGS. 3A and 3B.
Figure 4B:
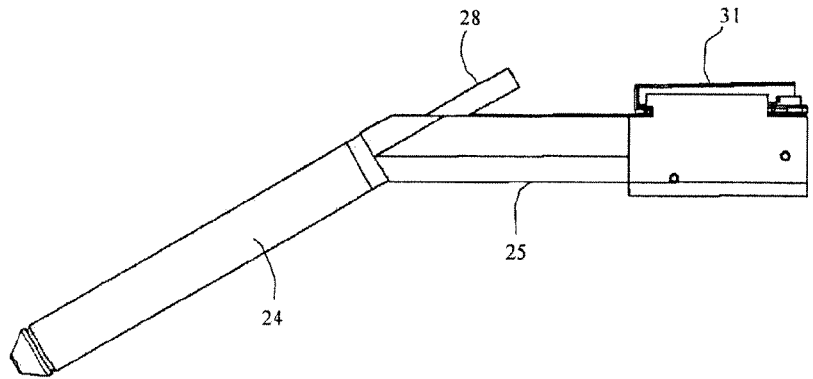
FIG. 4B illustrates a super-side view of a disposable needle-sleeve and needle-sleeve-block of FIGS. 3A, 3B, and 4A.
Figure 4C:
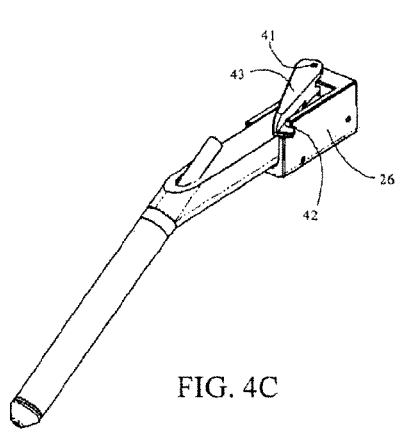
FIGS. 4C and 4D illustrate a the snap-in mechanism of the disposable needle block of FIGS. 4A and 4B.
Figure 4D:
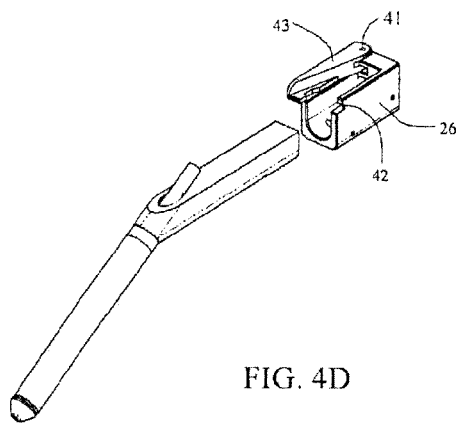

A specific embodiment of a needle-sleeve 24 and needle-sleeve-block 25 is shown in FIGS. 4A-4D. FIG. 4A illustrates the disposable needle-sleeve and needle-sleeve-block in cross sectional view and FIG. 4B illustrates a super side view of the disposable needle-sleeve and needle-sleeve-block. The needle-sleeve 24 incorporates an outer tube 27, which is sealed on its distal end by a seal-stop 29, or a molded plastic ending, not further shown here. On the proximal side of the needle-sleeve 24 the needle-sleeve-block 25 seals the outer tube 27. An inner tube 28 penetrated through the entire length of the needle-sleeve 24. The hollow space 30 within the outer tube 27 is therefore sealed. This hollow space 30 can be filled with any contrast giving agent. In a specific embodiment, hollow space 30 can be filled with a MR positive contrast producing media with short $T_1$, $T_2$ or $T_2^*$ relaxation time. Examples of such media include Gd-DTPA (Gadolinium-diethylene-triaminepentacetic acid) and vitamin E. This contrast producing agent can allow the needle-sleeve 24 to be located easily under MR imaging. Very fast sequences can be used to show the needle guide. The section plane in which the biopsy should take place can be defined such that real time imaging in this plane can allow movement of the needle guide until it is perfectly lined up with the lesion. The needle guide can be fixed in this position and the biopsy can be taken outside the magnet.

The needle-sleeve-lock-in mechanism 26 allows a fast, safe and easy connection of the needle holder in the positioning device. Mechanical fixation 41 allows a precise lock-in in the longitudinal axis of the needle-sleeve-block 25. The mechanical fixation mechanism 42 has a squared cross section to prevent rotation of the needle-sleeve-block 25. The locking lever 43 fits into the mechanical fixation 41 at the opposite site.

The subject invention also relates to other techniques to make the needle sleeve visible for the MRI scanner. Fiducial markers, or other markers that use for example overhauser or electron spin can be incorporated. Two or three of these markers can exactly define the position of the needle sleeve and the way the needle will go. To save time it is possible to take a high resolution 3-D-image first and use the needle guide only to navigate. This has the advantage of fast nice pictures of the lesion in real time. For safety reasons it might be desirable to take at least one image with the needle guide in place.

The biopsy needle can slide through inner tube 28, which can be aligned parallel to the outer tube 27. The inner diameter and length of tube 28 can match the outer diameter of the biopsy needle used. Typically the inner diameter is 8 to 16 G (gauge) or 1.7 to 3.0 mm. The needle-sleeve-block 25 with needle-sleeve 24 can be adapted to the needle-sleeve-holder 22 of the reusable prostate-biopsy system by, for example, a snap-on mechanism 31. For better orientation, the needle sleeve block can be filled with material which can produce contrast to show up in the image and indicate the axis of rotation of screw 50. In a specific embodiment, the needle sleeve can be made of materials substantially invisible to magnetic resonance imaging and a needle which is visible can be used.

The system incorporating the needle-sleeve 24 and its subparts, the needle-sleeve-block 25, and the snap-on mechanism 31 can be made as one disposable part. This system can utilize plastic parts. Examples of plastic which can be utilized include but are not limited to, PE, PP, PU, PEEK or TEFLON (i.e. polytetrafluoroethylene (PTFE)). Ceramic or low artifact giving metals, such as titanium and titanium-alloys can also be used.

Figure 5A:
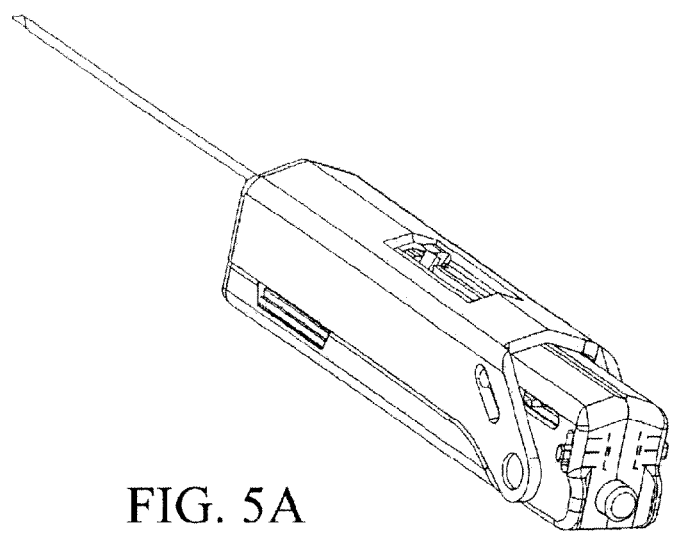
FIG. 5A illustrates a disposable biopsy needle which can be used with an embodiment of the subject invention.

FIG. 5A shows a typical, disposable, fully automatic biopsy needle as used for this prostate biopsy device. The needle itself can be made out of a MR visible titanium alloy as described for instance in U.S. Pat. Nos. 6,120,517 or 5,895,401. Other surgical tools like the one in U.S. Pat. No. 6,238,355 can be inserted as well.

Figure 5B:
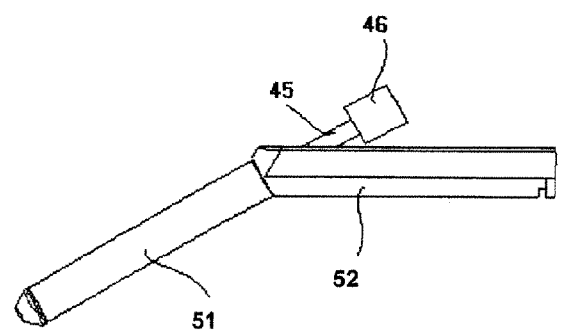
FIG. 5B illustrates a needle guide with depth control which can be incorporated with an embodiment of the subject invention.

FIG. 5B shows a needle guide with depth control. The hub-tube 45 is coaxial and penetrates through the needle-sleeve 51 and has a stopper 46 on its proximal end. This hub-tube 45 shortens or lengthens the inner tube 28 of the needle-sleeve 51. Hence, if a needle, such as shown in FIG. 5A, penetrates through the inner-tube 28 it will have to stop at the stopper 46 and therefore can penetrate to a defined depth. This hub-tube 45 can be locked in position by a lock-in mechanism not shown herein.

Figure 5C:
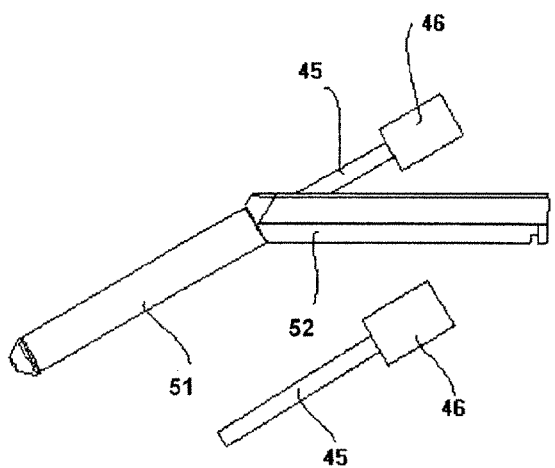
FIG. 5C illustrates a hub-tube and stopper located at a different position with respect to needle block 51 than shown in FIG. 5B and shows a hub-tube 45 and stopper 46 outside of the needle block 51 for illustration purposes.

FIG. 5C shows the hub-tube 45 and stopper 46 located at a different position with respect to needle sleeve 51 than shown in FIG. 5B and shows a hub-tube 45 and stopper 46 outside of the needle sleeve 51 for illustration purposes.

Figure 6:
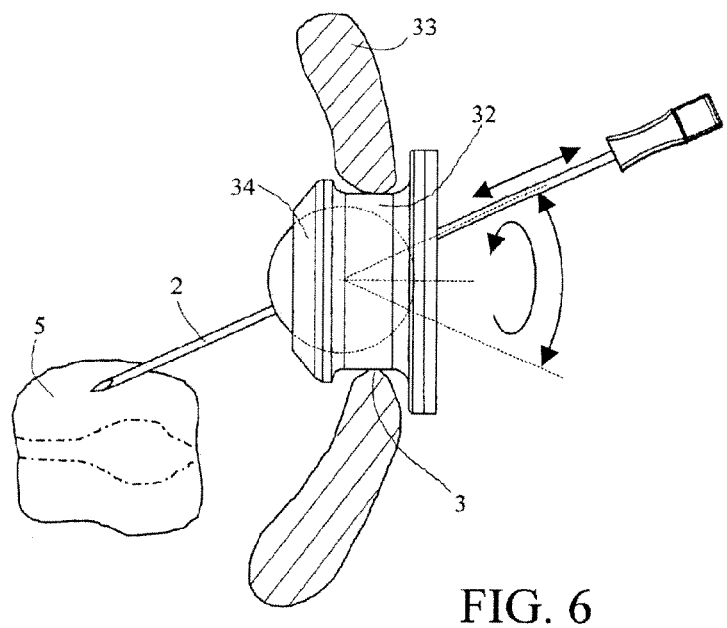
FIG. 6 illustrates a cross-sectional view of a straight biopsy device in accordance with the subject invention, which is attached to a patient's body.
Figure 7:
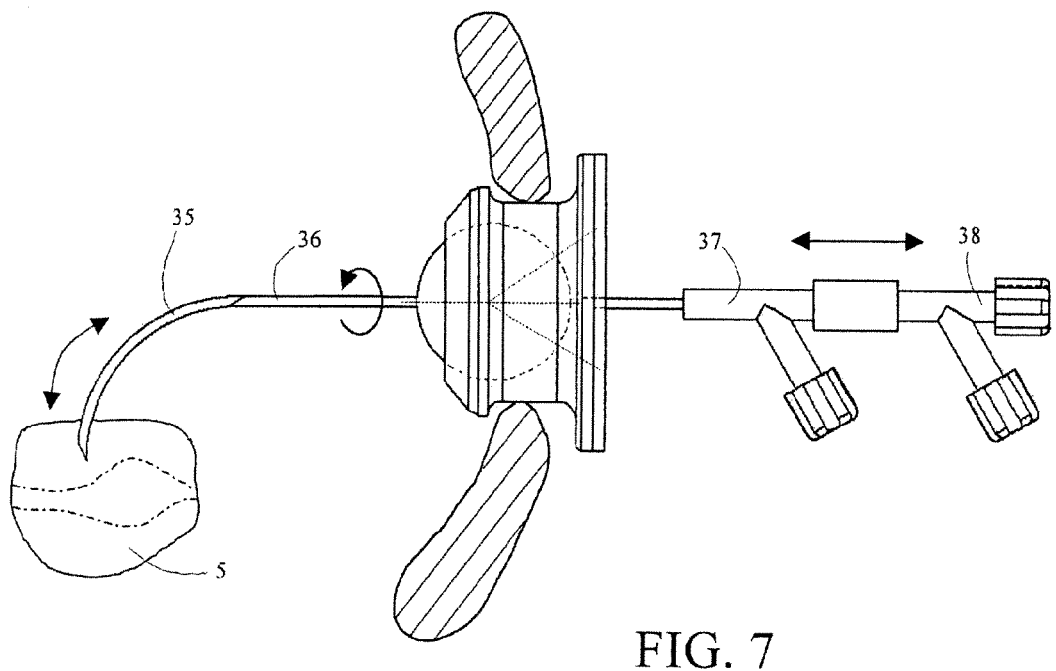
FIG. 7 illustrates a cross-sectional view of a curved biopsy device in accordance with the subject invention, which is attached to the patient's body.

Another specific embodiment of the subject invention is shown in FIG. 6. The biopsy needle 2 is penetrating through the positioning system 32, which itself is only mounted to the patient 33 by clamping in the anus 3. The positioning system 32 comprises a ball-and-socket-joint 34, which allows a full angulated movement of the biopsy needle 2, as shown by curved arrows in FIG. 6. This positioning system 32 can be a disposable device, and can be made of MR compatible materials, such as PE, PP, PU, PEEK or TEFLON (PTFE). Ceramic or low artifact giving metals, such as titanium and titanium-alloys can also be used. FIG. 7 shows the same device with a needle 35, which is pre-bent and curves in a given direction when pushed out of a straight rigid needle 36. The curved needle 35 can be made out of, for example, super-elastic nickel-titanium (NiTi), the rigid and straight needle 36 can be made out of a titanium alloy, such as described in U.S. Pat. No. 6,238,355. Outer needle 36 is attached to grip 37, and needle 35 is attached to grip 38. By grasping grip 38 with one hand and grip 37 with the other hand and pushing the one hand, and therefore grip 38, against the other hand, and therefore grip 37, needle 35 will be pushed out of needle 36 and will bend, as shown with the arrows.

Figure 9:
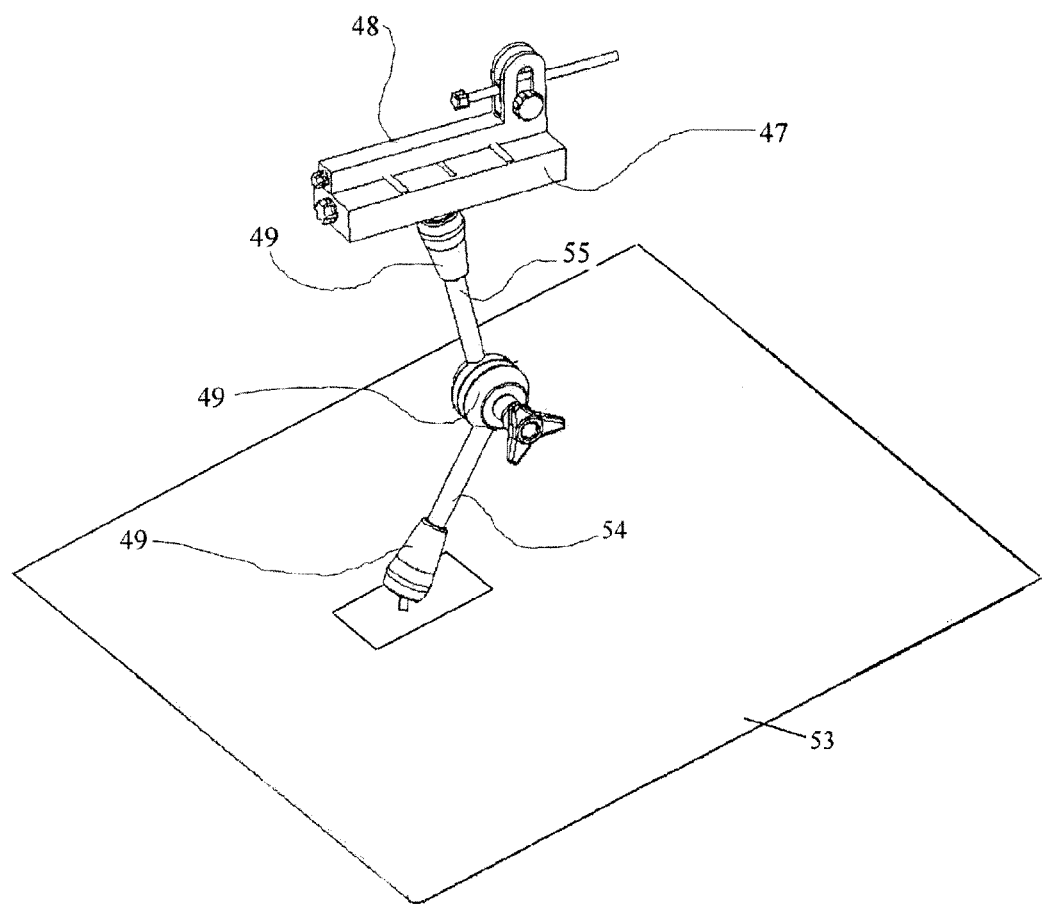
FIG. 9 illustrates a three dimensional view of another specific embodiment of the subject invention.

FIG. 9 shows an alternative version of the prostate biopsy system. The needle plate 47 holds the biopsy device, which can be automated and driven by an MR compatible piezoelectric motor, for instance as shown in U.S. Pat. No. 6,274,965. This mechanism is posted on an upper arm 55, lower arm 54 and a base plate 53, all to be locked in defined positions by locking mechanism 49.

EXAMPLE 1

This example describes a method for affecting a biopsy in accordance with the subject invention. In a specific embodiment, the subject prostate-biopsy-device can be operated in conjunction with a body faced array coil taking 6 to 8 samples, for example, by implementing the following:

Position the patient and the subject prostate-biopsy-device. Lay the patient prone on the stabilization pillow.

Install the body faced array coil, and the arm of the prostate biopsy device.

Insert the needle-sleeve through the anus onto the inner wall of the intestine posterior to the prostate (left apical corner of the prostate a).

Move the patient with device in the MR magnet and perform a first control scan (axial through prostate and needle sleeve).

Reposition the needle-sleeve if needed by moving the arm of the device from outside by using the sticks or move the patient out of the magnet and reposition manually the appropriate screws.

Measure the depth of the lesion in the prostate via another MR scan. If position is right move the patient out of magnet, introduce the biopsy needle through the needle sleeve into the prostate, and fire the biopsy needle to do the biopsy, or move the patient out of the magnet, introduce the biopsy through the needle sleeve into the prostate, fire the needle, and take a control image with the needle in place. Push out the needle notch, move the patient back into the MR magnet to make a controlling scan, and move the patient out of the magnet, to fire the biopsy needle to do the biopsy. (Or move the patient out of the magnet, introduce the biopsy needle through the needle sleeve into the prostate, drive the patient back into the MR magnet, and fire the biopsy needle to do the biopsy by using a stick from outside to operate the needle.) Alternatively, the hub-tube 45 of the device can be repositioned, so that the needle only penetrates to a certain depth.

Figure 8:
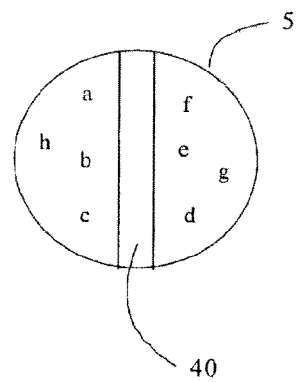
FIG. 8 illustrates the different biopsy locations in the prostate gland.

Take out the first sample. Move the sliding part of the lower arm 20 by turning adjustment screw 19 to position the needle sleeve in the middle b (referring to FIG. 8) of the left half of prostate 5 and to the end c (referring to FIG. 8) of the prostate 5 to take a biopsy from each position. Position the needle guide at the right side of the prostate 5 d (referring to FIG. 8) and take a control image. If the position is correct the patient is moved out of the magnet again and the next tree biopsies d, e, f, (referring to FIG. 8) can be taken from the right side of the prostate in the same way as the left. For biopsies of special regions or additional lateral biopsies, the needle guide has to be positioned new and a control image has to be taken.

The procedure described in this example allows a caregiver to take only two to four images to perform safe and fast biopsies with good control of the needle position. T2 weighted sequences can be used to view the prostate 5. After giving contrast media T1, weighted FLASH 3D sequences (SIEMENS 1.5T) can be used. For the intervention itself, a HASTE sequence or a T1 weighted Spin Echo sequence can be used. In a 0.2 T SIEMENS MR tomographer, imaging was accomplished using a FLASH 2D-Sequence (TR/TE=100/9: 70Grad), T2-SE (TR/TE=100/9; 70Grad), and a FISP-Rotated-Keyhole-Sequence (TR/TE=18/8; 90Grad).

EXAMPLE 2

Embodiments of the subject invention can use the KM-filled needle guide to be detected under MRI and to be used to guide instruments under MRI. The needle guide can have different sizes and shapes that allow better detection or better recognition under MRI. The shape of the cavity that is filled can have, for example, a round shape, a cylindrical shape with a central aperture to put the needle through, or an irregular shape that can allow detection of all three degrees of freedom, as well as rotation. The use of different shapes can allow differentiation of needle guides from each other if there is more than one needle guide used at the same a time. In addition, software can be used to automatically detect the position of the needle sleeve and to use this information to control the MRI scanner. Transfer of this information to the scanner to acquire the MR-signal of the needle sleeve can be enhanced by adding self-resonating LC-circuits or small active coils. Both techniques can help to detect the needle guide with the MR-scanner and automatically detect the instrument track. Resonating or active coils of different size and shape can help differentiate the needle sleeves and make localization faster and more accurate.

To position an instrument in a moving organ such as a liver or a lung, a more flexible holding arm can be utilized and a connector for interconnection with sterile positioning units can be incorporated.

An embodiment of the subject invention has a base that can be a base plate or a fixation on the MR-table. Further, there is a flexible positioning arm with two rotating ball-joints at the ends, one joint in the middle, and a central clamping mechanism. The distal end has a connector to allow connection to different sterile positioning units. This connection can be designed so that a plastic drape can be placed over the holding arm so that the conical part of the connector can be pushed through the plastic drape. This allows a sterile drape holding arm to be connected with a sterile positioning arm.

In this case, the positioning unit carries an adjustable ball-shaped needle guide that is pushed against the skin and can allow insertion and guiding of an instrument. The S-shaped fixation arms allow the ball to be placed directly on the skin and to have area for a loop-coil to improve images in the region of interest. This imaging coil can also be integrated in the fixation arms or connected to them. This coil can also be used as a positioning coil as it is close to the needle guide and can detect the position and direction of the needle sleeve by using a special sequence that correlates with the filling and configuration of the needle guide to give clear signals.

An embodiment of the subject invention can allow clamping of the bass-shaped needle guide, which can contain KM filling or can be connected to a needle guide of, for example, a cylindrical or other shape. The screw allows free rotation and clamping of the ball. If the screw is opened further, the ball can be released completely to allow free motion by an easy-release mechanism. For example, the ball can take disposable needle sleeves that are currently used for breast biopsies with integrated clamping, and can also take bone biopsy devices or instruments such as endoscopes.

It is possible to steer the MR-imaging plane by the needle guide with real time imaging. The needle guide is detected by an automated detection software, as known in the art, which can provide the MR scanner the direction and position of the imaging plane. If the instrument is in the correct position, the MR scanner can automatically generate a control scan that shows the instrument and the surrounding anatomy.

It is also possible to use the MR scanner as a navigation system to detect the needle guide and to overlay the theoretical position from a prior detected dataset. This can allow pre-adjustment and the ability to take a confirmation scan to see if the instrument can be inserted safely.

MR-detectable markers can be integrated in the holding arm, the connector, the positioning unit, in the needle guide, or integrated in the Instrument. Techniques for connecting markers with the instruments is well known in the art and can be utilized in accordance with the subject invention.

The holding arm can carry different positioning systems, such as one for a prostate or one with the ball-shaped needle guide for a liver as described above. The holding arm can also carry a y-x positioning unit or a grid-plate. The conical connector can carry a frame that may have an integrated coil and can carry the grid-plate or can carry the plates for y-x positioning.

The frame can carry fiducial markers that can be recognized by software, such as DynaCad™, to determine the exact needle position or needle guide position, which can be used to adjust and to visualize the needle track before the needle is inserted.

The fast connector allows the exchange of positioning units as well as the use of marker-plates to form different navigation systems, and allow the combination of these solutions. In this way, it is possible to define the position with an optical or other navigation system outside the magnet or to reference the arm position and to make adjustments with the positioning unit.

In addition, to make these positioning capabilities more effective, it is often desirable to have very little patient movement. This can be achieved by using a vacuum mattress to fix the extremities, for example. This mattress can be connected to the base of the holding arm.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A device for performing a biopsy, comprising:
   a needle sleeve configured to pass a biopsy needle therethrough, the needle sleeve being visible during magnetic resonance imaging, the needle sleeve being shaped such that a distal end of the needle sleeve is configured to be guided through an anus of the patient onto an inner wall of an intestine behind a prostate of the patient; and
   a needle sleeve holder configured to position the needle sleeve in three dimensions.

2. The device according to claim 1, wherein the needle sleeve holder allows the needle sleeve to be moved in all three dimensions concurrently.

3. The device according to claim 1, wherein the needle sleeve is configured to be adjusted and clamped during magnetic resonance imaging.

4. The device according to claim 1, wherein the needle sleeve is constructed of a material that provides an MR-signal.

5. The device according to claim 1, wherein the needle sleeve holder comprises a snap on mechanism.

6. The device according to claim 5, wherein the snap on mechanism has a positive fit for axial and transversal fixation and a mechanical lock for a third dimension.

7. The device according to claim 1, wherein the needle sleeve is adapted to accommodate different needle diameters and lengths.

8. The device according to claim 1, wherein the needle sleeve holder is made of MR compatible materials.

9. The device according to claim 8, wherein the needle sleeve holder is made of materials selected from the group consisting of: polyethylene, polypropylene, polyurethane, polyester ether keyton, polytetrafluoroethylene, ceramic, titanium and titanium-alloys.

10. The device according to claim 1, wherein the needle sleeve holder includes:
    inner and outer sleeves that are invisible under magnetic resonance imaging, the inner and outer sleeves defining an annular hollow space therebetween; and
    a seal stop mounted to distal ends of the inner and outer sleeves to close the annular hollow space to define magnetic resonance imagable contrast agent receiving receiver, the seal stop including an aperture aligned with the inner tube such that the biopsy needle passes through the inner tube and the seal stop aperture.

11. A device for performing a biopsy comprising:
    a needle sleeve including an outer tube and an inner tube penetrating through an entire length of the needle sleeve, an annular space being defined between the outer tube and the inner tube, the annular space containing an MR agent which allows the needle sleeve to be visible during MR imaging, the inner tube being configured such that a biopsy needle is insertable through and guided by the needle sleeve, the needle sleeve being shaped for penetration of a patient during biopsy; and
    a needle sleeve holder configured to allow an operator to position the needle sleeve in three dimensions in an MR imaging region while the operator is outside of the MR imaging region.

12. The device according to claim 11, further comprising:
    a positioning device which positions the patient with respect to the needle sleeve holder.

13. The device according to claim 12, wherein the positioning device stabilizes the patient in a prone position.

14. The device according to claim 11, further including:
    a remote control device with which the operator positions the needle sleeve holder.

15. The device according to claim 14, wherein the remote control includes ultrasound motors.

16. The device according to claim 14, wherein the remote control includes one or more mechanical extension sticks.

17. The device according to claim 11, further including:
    a needle sleeve block to which the inner tube and the outer tube are mounted, the needle sleeve block being configured to be received in a positioning arm assembly.

18. The device according to claim 17, wherein the positioning arm assembly includes a needle sleeve block locking mechanism which receives the needle sleeve block, the needle sleeve block locking mechanism including a latch which releasably latches the needle sleeve block into the needle sleeve locking mechanism.

19. The device according to claim 18, further including a positioning device for positioning the needle sleeve, the positioning device including:
    a lower arm along which a sliding part moves to position the needle device in a first direction; and
    an upper arm on which the needle sleeve holder is slidably movable.

20. The device according to claim 11, further including:
    a needle sleeve block to which the needle sleeve is mounted, the needle sleeve block being configured to be received in a positioning arm assembly.

21. A device for performing a biopsy, comprising:
    a needle sleeve, wherein the needle sleeve is adapted to allow a needle to pass therethrough, wherein the needle sleeve is visible under magnetic resonance imaging, wherein the needle sleeve is shaped for penetration of a patient during biopsy such that a distal end of the needle sleeve is capable of being guided through an anus of the patient onto an inner wall of an intestine of the patient behind the prostrate of the patient; and
    a needle sleeve holder, wherein the needle sleeve holder allows an operator to position the needle sleeve in three dimensions,
    a positioning device, wherein the positioning device allows positioning of the patient with respect to the needle sleeve holder,
    wherein the positioning device provides cushion to the patient.

22. A device for performing a biopsy, comprising:
    a needle sleeve configured to pass a biopsy therethrough, the needle sleeve being visible during magnetic resonance imaging, the needle sleeve being shaped for penetration of a patient during a biopsy to position a distal end of the needle sleeve is adjacent internal tissue to be biopsied;
    a needle sleeve block to which the needle sleeve is mounted, the needle sleeve block being configured to be received in a positioning arm assembly, the positioning arm assembly including a needle sleeve locking mechanism which receives the needle sleeve block, the needle sleeve locking mechanism including a latch which releasably latches the needle sleeve block into the needle sleeve locking mechanism.

23. The device according to claim 22, wherein the needle sleeve comprises one or more MR-visible markers.

24. The device according to claim 22, further including a positioning device for positioning the needle sleeve, the positioning device including:
    a lower arm along which a sliding part moves to position the needle device in a first direction; and
    an upper arm on which the needle sleeve holder is slidably movable.

25. The device according to claim 22, further including:
a needle sleeve holder which positions the needle sleeve block in three dimensions.

26. The device according to claim 25, further including:
a needle locking mechanism mounted with the needle sleeve holder, the needle sleeve locking mechanism releasably locking the needle sleeve block to the needle sleeve holder.

27. The device according to claim 26, further including:
a needle sleeve block on which the needle sleeve is mounted, the needle sleeve block being configured to be releasably received in the needle sleeve locking mechanism.

28. A device for performing a biopsy, comprising:
a needle sleeve configured to pass a biopsy needle therethrough, the needle sleeve defining an elongated hollow space which receives a magnetic resonance contrast agent which is visible during magnetic resonance imaging, the hollow space extending parallel to the biopsy needle passing through the needle sleeve to indicate a trajectory of the biopsy needle, the needle sleeve being shaped for penetration of a patient during a biopsy to position a distal end of the needle sleeve adjacent internal tissue to be biopsied; and
a needle sleeve holder configured to position the needle sleeve in three dimensions.

29. The device according to claim 28, further including:
a needle sleeve locking mechanism mounted with the needle sleeve holder, the needle sleeve locking mechanism releasably locking the needle sleeve to the needle sleeve holder.

30. The device according to claim 29, further including:
a needle sleeve block on which the needle sleeve is mounted, the needle sleeve block being configured to be releasably received in the needle sleeve locking mechanism.

31. The device according to claim 28, wherein the hollow space extends concentrically around the biopsy needle passing through the needle sleeve.

* * * * *